United States Patent [19] [11] 4,138,585
Adams [45] Feb. 6, 1979

[54] PROCESS FOR PREPARING N-ALKOXYCARBONYL-N-ALKYLCYANAMIDE

[75] Inventor: Charles D. Adams, Newark, Del.

[73] Assignee: E. I. Du Pont de Nemours and Company, Wilmington, Del.

[21] Appl. No.: 874,354

[22] Filed: Feb. 1, 1978

[51] Int. Cl.$^2$ ............................................. C07C 125/06
[52] U.S. Cl. ..................................................... 560/159
[58] Field of Search .......................................... 560/159

[56] References Cited

U.S. PATENT DOCUMENTS

| | | | |
|---|---|---|---|
| 3,190,919 | 6/1965 | Swanson | 260/501.15 |
| 3,850,924 | 11/1974 | Fuchs et al. | 71/93 |
| 3,902,887 | 9/1975 | Lin | 71/93 |
| 3,983,116 | 9/1976 | Lin | 71/93 |
| 3,992,432 | 11/1976 | Napier | 260/465.1 |

OTHER PUBLICATIONS

Berichte, vol. 62, pp. 1393–1394 (1929).
Jones, Aldrichimia Acta, vol. 9, No. 3, pp. 35–45, 1976.

Primary Examiner—Howard T. Mars
Assistant Examiner—G. T. Breitenstein

[57] ABSTRACT

Quaternary ammonium salts act as phase transfer catalysts when present in reactions of alkoxycarbonylcyanamide with di-$C_{1-3}$ alkyl sulfate.

7 Claims, No Drawings

PROCESS FOR PREPARING N-ALKOXYCARBONYL-N-ALKYLCYANAMIDE

This invention relates to an improvement in a process for preparing N-alkoxycarbonyl-N-alkylcyanamide.

BACKGROUND OF THE INVENTION

French Pat. No. 7,318,733 discloses and claims a process for preparing 3-substituted-1-methyl-6-substituted amino-s-triazine-2,4(1H,3H) diones by a reaction sequence which includes the step of contacting an alkoxycarbonylcyanamide with an alkylating agent to form an N-alkoxycarbonyl-N-alkylcyanamide as an intermediate. In particular, the sodium salt of ethoxycarbonyl cyanamide in aqueous solution can be reacted with dimethyl sulfate (DMS) to obtain N-ethoxycarbonyl-N-methylcyanamide. As the desired reaction proceeds, the DMS also reacts with sodium chloride which is present in the original aqueous solution to form methyl chloride as an undesirable by-product. Because of the methyl chloride formation, which consumes a significant amount of DMS, a 50% excess of DMS must be added to obtain an 81% batch yield of N-ethoxycarbonyl-N-methylcyanamide. Also described is a continuous, counter-current reaction process which provides improved yields and requires a smaller excess of DMS.

Slotta and Tschesche, Ber., 62, 1393 (1929) obtained a 58% yield when the sodium salt of ethoxycarbonylcyanamide was reacted with a 60% excess of DMS. No sodium chloride was present in the experiment.

Jones, Aldrichimia Acta, Vol. 9, No. 3, pp. 35-45 (1976) describes the application of phase transfer catalysis in organic synthesis. None of the references, however, suggest the desirability of employing a catalyst in the intermediate methylation step of the reaction sequence followed for preparing 3-substituted-1-methyl-6-substituted amino-s-triazine-2,4(1H,3H) diones.

SUMMARY OF THE INVENTION

The present invention provides an improvement in a process for preparing N-alkoxycarbonyl-N-alkylcyanamides of the formula

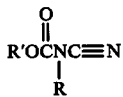

wherein R is alkyl of 1-3 carbon atoms and R' is alkyl of 1-3 carbon atoms by mixing an aqueous solution of an alkali or alkaline earth metal salt of N-alkoxycarbonylcyanamide with a di-$C_{1-3}$ alkyl sulfate, the improvement comprising mixing said aqueous solution with said di-$C_{1-3}$ alkyl sulfate in the presence of at least about 0.1 mole % of quaternary hydrocarbyl ammonium ions per mole of N-alkoxycarbonylcyanamide, the hydrocarbyl moieties being selected from the group consisting of alkyl, aryl, alkaryl and aralkyl groups having a total carbon content of from 7 to 60 carbon atoms per ion.

Preferred for reduced cost and low by-product formation is the improvement in which the hydrocarbyl moieties are selected from the group consisting of alkyl, aryl, alkaryl and aralkyl groups having a total carbon content of from 10 to 40 carbon atoms per ion.

More preferred for reduced production cost and/or low by-product formation and convenience is the improvement in which the hydrocarbyl moieties are selected from the group consisting of alkyl, aryl, alkaryl and aralkyl groups having a total carbon content of from 12 to 20 carbon atoms per ion, the di-$C_{1-3}$ alkyl sulfate is dimethyl sulfate, and R' is ethyl.

Most preferred for operability and convenience is the improvement in which the hydrocarbyl ammonium ions are formed "in situ" by addition to the reaction mass of a compound selected from the group consisting of primary, secondary and tertiary amines.

The quaternary ammonium ions, when present in the reaction at low levels, e.g., 0.1 to 2.0 mole %, operate to improve yields, reduce reaction time, allow lower reaction temperatures and reduce the formation of methyl chloride.

DETAILED DESCRIPTION OF THE INVENTION

In the manufacture of 3-substituted-1-methyl-6-substituted amino-s-triazine-2,4(1H,3H) diones and in particular 3-cyclohexyl-1-methyl-6-dimethylamino-s-triazine-2,4(1H,3H) dione, salts of alkyl cyanocarbamates, alternatively named alkoxycarbonylcyanamides, are prepared as described in French Pat. No. 7,318,733, the teachings of which are incorporated herein by reference. The particular reaction may be described by the following equation.

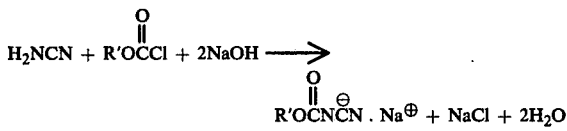

The alkoxycarbonylcyanamide is then reacted with dimethyl sulfate as described by the following equation to form the appropriate N-alkoxycarbonyl-N-methyl cyanamide as an intermediate.

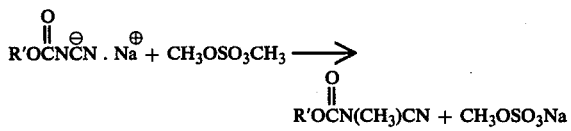

In the preparation of N-ethoxycarbonyl-N-methylcyanamide, for example, the sodium salt of N-ethoxycarbonylcyanamide in aqueous solution can be mixed with dimethyl sulfate (DMS) to yield N-ethoxycarbonyl-N-methylcyanamide at atmospheric pressure and at a temperature in the range of about 10° to 70° C.

When the DMS is added to the aqueous solution, a second, nonaqueous (oil) phase is formed almost immediately. Initially the nonaqueous layer is a mixture of N-ethoxycarbonyl-N-methylcyanamide and DMS with a high proportion of the latter. As reaction proceeds, the relative amount of DMS in the nonaqueous layer declines to trace levels. Since DMS has a low solubility in water, i.e., about 2.7% and an even lower solubility in a salt solution, the DMS distribution coefficient is such that at any given stage of the reaction, most of the DMS in the reaction mass is present in the oil phase, and only a relatively small amount is present in the aqueous phase. However, it appears that the reaction occurs only in the aqueous phase because this is the only phase which contains ethoxycarbonylcyanamide anion. A possible reaction mechanism may be seen below. It may also be seen that sodium chloride can react with DMS to form methyl chloride, an undesirable by-product.

Because of the methyl chloride formation, a 50% excess of DMS must be used to obtain an 81% batch yield of N-ethoxycarbonyl-N-methylcyanamide. It is stated in French Pat. No. 7,318,733, however, that a better yield can be obtained by resorting to a complicated, continuous counter-current reaction scheme.

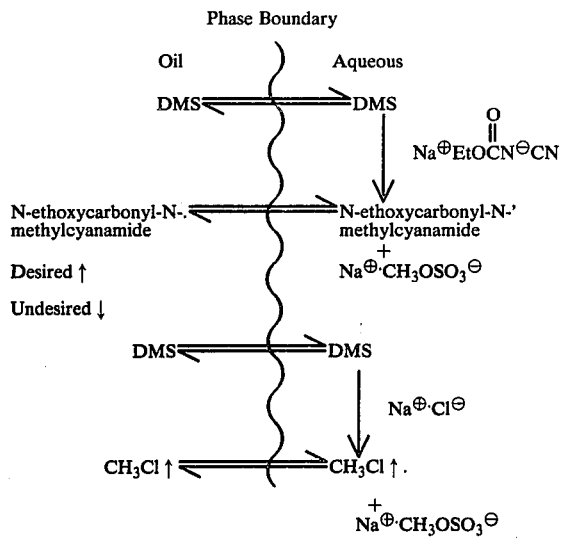

According to the instant invention, the presence of large molecular weight quaternary ammonium cations, i.e., about 0.1 to about 2.0 mole %, results in the transfer of ethoxycarbonylcyanamide (ECC) anions from the aqueous phase to the oil phase where DMS concentration is highest. It has also been discovered that an adjustment of the reaction temperature to about 25° C. substantially reduces the water phase reaction rate between chloride ion and DMS relative to the water phase reaction rate between ECC anion and DMS. The net result is that DMS has an increased opportunity to react with ECC anion and a decreased opportunity to react with chloride ion when quaternary ammonium ions are present. This simple addition of a quaternary ammonium ion provides equal or better yield benefits than the complicated and expensive continuous counter-current reaction scheme described in the prior art. The possible new reaction mechanism may be seen below where $Q^\oplus$ represents the quaternary ammonium cation.

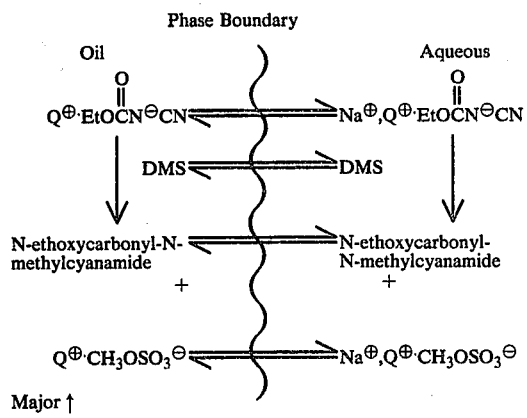

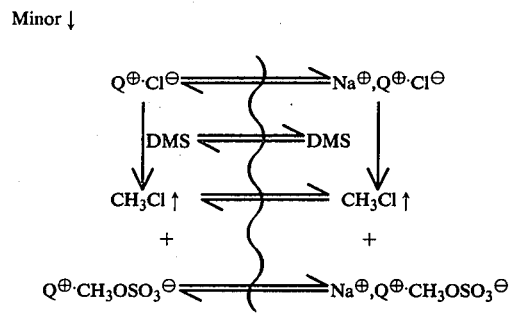

In a preferred embodiment of the instant invention an aqueous solution of an ethoxycarbonylcyanamide salt is mixed with di-$C_{1-3}$ alkyl sulfate in the presence of a quaternary ammonium salt, such as tetrabutyl ammonium chloride, according to the following reaction sequence:

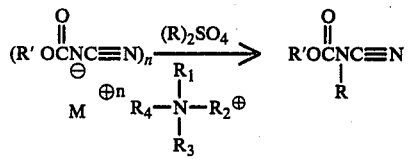

wherein
$M^+$ is alkali or alkaline earth metal ion;
n is 1 or 2;
R' is ethyl;
R is alkyl of 1–3 carbon atoms; and
$R_1$, $R_2$, $R_3$ and $R_4$ are selected from the group consisting of alkyl, aryl, alkaryl and aralkyl groups having a total carbon content of from 7 to 60 carbon atoms per ion.

In a second preferred embodiment of this invention the quaternary ammonium ions are formed in situ by addition to the reaction mass of a compound selected from the group consisting of primary, secondary and tertiary amines. For example, trialkylamines such as triisopentylamine and tri-n-butylamine are methylated in situ by dimethyl sulfate to form trialkylmethylammonium methyl sulfate.

The in situ reaction for primary, secondary, and tertiary amines may be described, respectively, by the following equations.

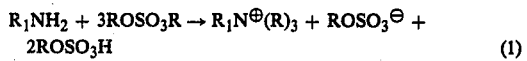  (1)

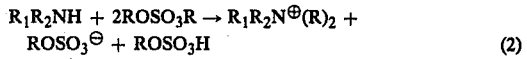  (2)

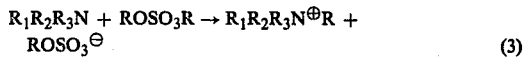  (3)

where $R_1$, $R_2$ and $R_3$ are alkyl, aryl, alkaryl and aralkyl and R is $C_1$ to $C_3$ alkyl. In this embodiment the amine is added to the aqueous solution of ethoxycarbonylcyanamide salt before the di$C_1$–$C_3$ alkyl sulfate is added. When R in the foregoing reactions is $C_2$ or $C_3$ alkyl instead of methyl, the in situ-formed quaternary ammonium ion will contain the appropriate R group. Thus, any triazinediones made as described in French Pat. No. 76,13,377 will contain the subject R group at the 1-position instead of methyl.

The improved process of this invention can provide yields of up to 87% (cyanamide basis) with not more than a 15% excess of DMS. In addition, the formation of methyl chloride, a potential atmospheric pollutant, can be reduced by about 70%.

The following examples further illustrate the improved process of this invention.

EXAMPLE 1

Preparation of N-Ethoxycarbonyl-N-Methylcyanamide Using Tetrabutylammonium Chloride as Catalyst To a reaction flask was added 625 parts (6.55 moles) of 44% cyanamide and 750 parts of water. Simultaneous addition of ethyl chloroformate (710 parts, 6.55 moles) and 51% of NaOH (1008 parts, 12.9 moles) was begun. The separate addition rates were adjusted as required to maintain the pH as close to 7.0 as possible. External ice bath cooling was used to keep the temperature at or below 55° C. The final solution weight was 3078 parts and it contained approximately 377 parts of NaCl and 880 parts of the sodium salt of N-ethoxycarbonylcyanamide.

A 500 part aliquot of this solution (equivalent to 1.06 moles cyanamide) was added to a flask along with 3.0 parts (1.0 mole percent on a cyanamide basis) of tetrabutylammonium chloride. The addition of 133 parts (1.06 moles) of dimethyl sulfate was begun and continued during 10 minutes while the temperature was kept at 25° C. by external cooling.

Stirring was continued for another 1.25 hours; then, the layers were settled and decanted. The upper layer of N-ethoxycarbonyl-N-methylcyanamide weighed 119 parts and was 93.2% pure as determined by gas chromatographic analysis. This corresponds to an 81.7% yield based on cyanamide.

EXAMPLE 2

Preparation of N-Ethoxycarbonyl-N-Methylcyanamide Using Tri-iso-Pentylamine as Catalyst A second 500 part aliquot of the N-ethoxycarbonylcyanamide solution described in Example 1 was charged to a flask along with 2.4 parts (1.0 mole percent) of tri-iso-pentylamine. Dimethyl sulfate (133 parts) was added during 0.5 hour while the temperature was kept at 25° C. Stirring at 25° C. was continued for another 1.5 hours before the layers were settled and decanted. The upper layer of N-ethoxycarbonyl-N-methylcyanamide weighed 117 parts and was 93.4% pure as determined by gas chromatographic analysis. This corresponds to a yield based on cyanamide of 80.5%.

EXAMPLE 3

Preparation of N-Ethoxycarbonyl-N-Methylcyanamide Using Tetrabutylammonium Chloride as Catalyst A third 500 part aliquot of the N-ethoxycarbonylcyanamide solution described in Example 1 was charged to a flask along with 1.5 parts (0.50 mole %) of tetrabutylammonium chloride. Dimethylsulfate (153 parts) was added during 0.5 hour while the temperature was kept at 25° C. by external cooling. Stirring at 25° C. was continued for another 1.5 hours before the layers were settled and decanted. The upper layer of N-ethoxycarbonyl-N-methylcyanamide weighed 129 parts and was 92.4% pure as determined by gas chromatographic analysis. This corresponds to a yield based on cyanamide of 87.8%.

EXAMPLE 4

Preparation of N-Ethoxycarbonyl-N-Methylcyanamide Using Various Amines and Quaternaries as Catalysts Solutions of the Na salt of N-ethoxycarbonylcyanamide were prepared as described in Example 1. In some cases, 550 parts of 50% cyanamide and 825 parts of water were used instead of 625 parts of 44% cyanamide with 750 parts of water. Aliquots of these solutions were then reacted with dimethyl sulfate as described in Examples 1, 2 and 3 to make N-ethoxycarbonyl-N-methylcyanamide. The following table summarizes the results of these trials:

| TRAIL | CATALYST | MOLE % CATALYST (CYANAMIDE BASIS (%) | DMS-CYANAMIDE MOLE RATIO | TEMP. (° C) | % YIELD (CYANAMIDE BASIS (%) |
|---|---|---|---|---|---|
| 1 | Tri-n-octyl-n-propyl-ammonium chloride | 0.50 | 1.15 | 25 | 87.1 |
| 2 | Ethyldibenzylamine | " | " | " | 84.9 |
| 3 | n-Dodecyldimethyl-amine | " | " | " | 81.8 |
| 4 | Ethyldicyclohexyl-amine | " | " | " | 80.2 |
| 5 | Triethylamine | 1.0 | " | " | 71.2 |
| 6 | Benzyltriethyl-ammonium chloride | 0.97 | 1.00 | 45 | 65.1 |
| 7 | Tetrabutylammonium bromide | 0.43 | " | " | 72.4 |
| 8 | Tetrabutylammonium bromide | " | " | 25 | 80.0 |
| 9 | Tetrabutylammonium chloride | 0.85 | " | 45 | 76.7 |
| 10 | Tetrabutylammonium chloride | 1.0 | " | 15 | 82.3 |
| 11 | Tri-iso-octylamine | 0.13 | 1.15 | 25 | 76.5 |
| 12 | Tri-iso-octylamine | 0.19 | " | " | 79.8 |
| 13 | Tri-iso-octylamine | 0.25 | " | " | 81.0 |
| 14 | Tri-iso-octylamine | 0.50 | " | " | 85.5 |
| 15 | Tri-iso-octylamine | 1.0 | " | " | 87.9 |
| 16 | Di-n-octylamine | 0.50 | " | 10 | 61.4 |
| 17 | Di-n-octylamine | " | " | 20 | 80.9 |
| 18 | Di-n-octylamine | " | " | 25 | 82.3 |
| 19 | Di-n-octylamine | " | " | 30 | 83.4 |
| 20 | Di-n-octylamine | " | " | 40 | 80.1 |
| 21 | Tri-n-octylamine | 1.0 | 1.00 | 25 | 79.0 |
| 22 | Tri-n-octylamine | 0.50 | " | " | 76.1 |
| 23 | Tri-n-octylamine | " | 1.10 | " | 82.2 |

-continued

| TRAIL | CATALYST | MOLE % CATALYST (CYANAMIDE BASIS (%)) | DMS-CYANAMIDE MOLE RATIO | TEMP. (°C) | % YIELD (CYANAMIDE BASIS (%)) |
|---|---|---|---|---|---|
| 24 | Tri-n-octylamine | " | 1.15 | " | 86.1 |
| 25 | Tri-n-octylamine | " | 1.20 | " | 86.8 |
| 26 | Tri-n-butylamine | " | 1.15 | " | 81.9 |
| 27 | Tri-n-butylamine | 1.0 | " | " | 86.4 |
| 28 | Tri-n-butylamine | 1.5 | " | " | 87.3 |

What is claimed is:

1. In a process for preparing N-ethoxycarbonyl-N-alkylcyanamides of the formula

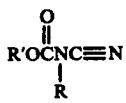

wherein R is alkyl of 1–3 carbon atoms and R' is alkyl of 1–3 carbon atoms by mixing an aqueous solution of an alkali or alkaline earth metal salt of N-alkoxycarbonyl-cyanamide with a di-$C_{1-3}$ alkyl sulfate, the improvement which comprises mixing said aqueous solution with said di-$C_{1-3}$ alkyl sulfate in the presence of at least about 0.1 mole % of quaternary hydrocarbyl ammonium ions per mole of N-alkoxycarbonylcyanamide, the hydrocarbyl moieties being selected from the group consisting of alkyl, aryl, alkaryl and aralkyl groups having a total carbon content of from 7 to 60 carbon atoms.

2. The process of claim 1 in which the hydrocarbyl moieties are selected from the group consisting of alkyl, aryl, alkaryl and aralkyl groups having a total carbon content of 10 to 50 carbon atoms.

3. The process of claim 1 in which the hydrocarbyl moieties are selected from the group consisting of alkyl, aryl, alkaryl and aralkyl groups having a total carbon content of 12 to 20 carbon atoms.

4. The process of claim 1 in which the hydrocarbyl ammonium ions are formed in situ by addition to the reaction mass of a compound selected from the group consisting of primary, secondary and tertiary amines.

5. The process of claim 4 in which the amine is tri-n-butylamine.

6. The process of claim 4 in which the amine is tri-iso-pentylamine.

7. The process of claim 1 in which the di-$C_{1-3}$ alkyl sulfate is dimethyl sulfate.

* * * * *